(12) United States Patent
Swick et al.

(10) Patent No.: US 10,987,376 B2
(45) Date of Patent: Apr. 27, 2021

(54) METHODS OF TREATING AND/OR PREVENTING NAIL DISORDERS AND/OR IMPROVING THE APPEARANCE OF A NAIL

(71) Applicant: CHESSON LABORATORY ASSOCIATES, INC., Durham, NC (US)

(72) Inventors: Lance L. Swick, Durham, NC (US); Scott E. Neuville, Durham, NC (US); Jerry S. Chesson, Durham, NC (US)

(73) Assignee: Chesson Laboratory Associates, Inc., Durham, NC (US)

( * ) Notice: Subject to any disclaimer, the term of this patent is extended or adjusted under 35 U.S.C. 154(b) by 481 days.

(21) Appl. No.: 14/891,311

(22) PCT Filed: May 13, 2014

(86) PCT No.: PCT/US2014/037835
§ 371 (c)(1),
(2) Date: Nov. 13, 2015

(87) PCT Pub. No.: WO2014/186355
PCT Pub. Date: Nov. 20, 2014

(65) Prior Publication Data
US 2016/0095811 A1 Apr. 7, 2016

Related U.S. Application Data

(60) Provisional application No. 61/824,566, filed on May 17, 2013.

(51) Int. Cl.
*A61K 31/785* (2006.01)
*A61K 8/84* (2006.01)
(Continued)

(52) U.S. Cl.
CPC .............. *A61K 31/785* (2013.01); *A61K 8/84* (2013.01); *A61K 8/86* (2013.01); *A61K 8/87* (2013.01);
(Continued)

(58) Field of Classification Search
None
See application file for complete search history.

(56) References Cited

U.S. PATENT DOCUMENTS 8,771,725 B2   7/2014   Chesson et al.
9,259,436 B2   2/2016   Chesson et al.
(Continued)

FOREIGN PATENT DOCUMENTS

WO        WO0245663        6/2002

OTHER PUBLICATIONS

Department of Health and Human Services, letter with attachment of 501(k) premarket notification of intent to market by Chesson Laboratory Associates; received May 3, 2012, date stamped May 17, 2012. (Year: 2012).*

(Continued)

*Primary Examiner* — Bethany P Barham
*Assistant Examiner* — Barbara S Frazier
(74) *Attorney, Agent, or Firm* — Olive Law Group, PLLC; Nathan P. Letts

(57) ABSTRACT

Systems and/or methods of treating and/or preventing nail disorders are disclosed herein. Also, disclosed herein are systems and/or methods of improving the appearance of a nail. A preferred embodiment of the present invention comprises a method of treating and/or preventing a nail disorder in a subject comprising topically applying a composition comprising a poly(urea-urethane)polymer and/or a poly (urea-urethane) pre-polymer to a nail of said subject, thereby treating and/or preventing said nail disorder.

12 Claims, 2 Drawing Sheets

(51) Int. Cl.
*A61K 8/86* (2006.01)
*A61K 8/87* (2006.01)
*A61K 47/34* (2017.01)
*A61Q 3/02* (2006.01)
*C09D 175/02* (2006.01)
*C09D 175/04* (2006.01)

(52) U.S. Cl.
CPC .............. *A61K 47/34* (2013.01); *A61Q 3/02* (2013.01); *C09D 175/02* (2013.01); *C09D 175/04* (2013.01)

(56) References Cited

U.S. PATENT DOCUMENTS

| 2001/0002253 | A1 | 5/2001 | Farer et al. | |
|---|---|---|---|---|
| 2002/0102222 | A1 | 8/2002 | Carrion et al. | |
| 2004/0071644 | A1* | 4/2004 | Mougin | A61K 8/37 424/61 |
| 2008/0253984 | A1 | 10/2008 | Kovacs et al. | |
| 2009/0098194 | A1* | 4/2009 | Chesson | A61K 8/87 424/447 |

OTHER PUBLICATIONS

Chesson Labs 510(K) Summary of Safety Effectiveness, Chesson Laboratory Associates, Inc., Nail Distrophy Product. May 17, 2012, url: http://accessdata.fda.gov/cdrh_docs/pdf12/K120059.pdf>entire article.

U.S. Appl. No. 12/103,353, filed Oct. 16, 2008, Chesson Lab Assoc.
Extended European Search Report issued in counterpart EP Application No. 14798102.1 dated Dec. 16, 2016 (four (4) pages).
Office Action issued in CA Application No. 2,912,538 dated May 17, 2018 (four (4) pages).
Swick, L. "510(k) Summary of Safety and Effectiveness" 2011, North Carolina. (six (6) pages).
Third Office Action issued in counterpart Chinese Application No. 201480028575.2 dated Nov. 1, 2018 (sixteen (16) pages).
Second Office Action issued in counterpart Chinese Application No. 201480028575.2 dated Feb. 1, 2018 (nine (9) pages).
First Office Action issued in counterpart Chinese Application No. 201480028575.2 dated Oct. 24, 2017 (five (5) pages).
Notice of Allowance issued in counterpart Canadian Patent Application No. 2,912,538 dated Jan. 22, 2019 (one (1) page).
Examination Report issued in counterpart Brunei Application No. BN/N/2015/0122 dated May 13, 2019 (eleven (11) pages).
Communication from New Zealand Intellectual Property Office issued in counterpart New Zealand Application No. 713964 dated May 25, 2020 (five (5) pages).
Vlahovic, T.C. "How to Treat Dystrophic Nails." Podiatry Today, Dec. 19, 2012, 42-46, vol. 26 (1), accessed Jun. 12, 2020. HMP Global, United States.
Nasir, A., et al. "Clinical Evaluation of Safety and Efficacy of a New Topical Treatment for Onychomycosis." J Drugs Dermatol., 2011, 1186-1191, vol. 10 (10). SanovaWorks, New York.
Chesson Laboratory Associates, Inc. (Feb. 2016). Nail Dystrophy Product—Nuvail™ [Material Safety Data Sheet]. Retrieved from https://www.medline.com/media/catalog/Docs/MSDS/MSD_SDSD70268.pdf on Jun. 12, 2020.

* cited by examiner

US 10,987,376 B2

METHODS OF TREATING AND/OR PREVENTING NAIL DISORDERS AND/OR IMPROVING THE APPEARANCE OF A NAIL

FIELD

The present invention generally relates to a system and/or method of treating and/or preventing nail disorders and/or a system and/or method of improving the appearance of a nail.

Nail disorders are medical conditions that can often be an embarrassment for an individual due to the appearance of the nail and may make the individual self-conscious. Treatments for nail disorders may include limiting external factors, such as activities that may cause or exacerbate the condition, which may not be suitable for the individual. Other treatments may include treating a possible underlying disease, but such treatments may be slow and may not be useful in improving the appearance of the nail.

The present invention may address previous shortcomings in the art by providing systems and/or methods of treating and/or preventing nail disorders and/or by providing systems and/or methods of improving the appearance of a nail.

SUMMARY

A first aspect of the present invention comprises a method of treating and/or preventing a nail disorder in a subject comprising topically applying a composition comprising a poly(urea-urethane)polymer and/or a poly(urea-urethane) pre-polymer to a nail of said subject, thereby treating and/or preventing said nail disorder.

A second aspect of the present invention comprises a method of improving the appearance of a nail of a subject comprising topically applying a composition comprising a poly(urea-urethane)polymer and/or a poly(urea-urethane) pre-polymer to said nail of said subject, thereby improving the appearance of said nail.

The foregoing and other aspects of the present invention will now be described in more detail herein.

DETAILED DESCRIPTION

Figure 1:
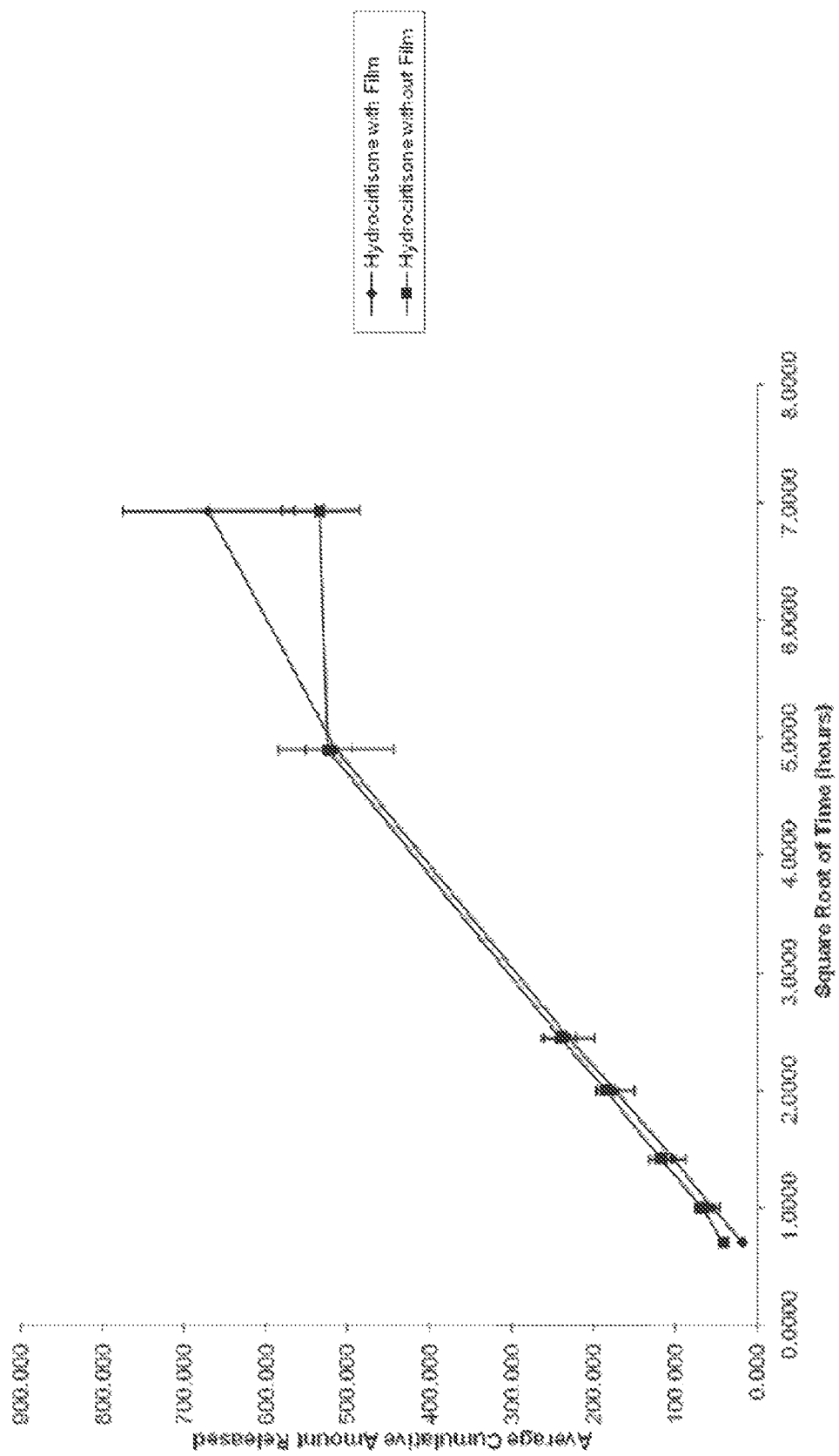
FIG. 1 shows a graph illustrating the release of composition comprising a hydrocortisone medicament through a nylon membrane according to embodiments of the invention.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 211 L03. Thus, the term "consisting essentially of" as used herein should not be interpreted as equivalent to "comprising."

The term "about," as used herein when referring to a measurable value such as an amount or concentration and the like, is meant to encompass variations of up to ±10%, ±5%, ±1%, ±0.5%, or even ±0.1% of the specified value as well as the specified value. For example, "about X" where X is the measurable value, is meant to include X as well as variations of up to ±10%, ±5%, ±1%, ±0.5%, or even ±0.1% of X. A range provided herein for a measurable value may include any other range and/or individual value therein.

Embodiments of the present invention describe systems and/or methods that may be used to treat and/or prevent a nail disorder in a nail of a subject. In some embodiments, a system and/or method of treating and/or preventing a nail disorder in a subject may comprise topically applying a composition described herein to a nail of the subject, thereby treating and/or preventing the nail disorder. In some embodiments, the composition may comprise a poly(urea-urethane) polymer and/or a poly(urea-urethane) pre-polymer. In certain embodiments, the composition may comprise a primary diamine optionally comprising a polyether segment; a secondary aromatic diamine; a polyisocyanate; and optionally, a polyol, and/or a reaction product thereof.

Exemplary nail disorders that may be treated and/or prevented using a system and/or method described herein include, but are not limited to, nail psoriasis, psoriatic nail dystrophy, onychia, onychiagryposis, onychia trophia, onychocryptosis, onychodystrophy, onychomycosis, onychogryposis, onycholysis, onychomadesis, onychauxis, onychorrhexis, onychoschizia, tines unguium, onychophosis, onychoptosis, paronychia, pseudomonas, pterygium and pterygium inversum unguis, koilonychia, subungual hematoma or other trauma to the nail, folic acid deficiency, sublingual hyperkeratosis, leukonychia, nail patella syndrome, melanonychia, protein deficiency, brittle and peeling nails, methyl methacrylate damaged nails, vitamin C deficiency, vitamin deficiency, tinea unguis, thinning nails associated with lichen planus, Raynaud's disease, nail dystrophy associated with rheumatoid arthritis, beau's lines, Mee's lines associated with certain kinds of poisoning, discoloration, lamellar splitting, longitudinal grooves and/or ridges, transverse grooves, pitting, soft nails, brittle nail syndrome, any combination thereof. In some embodiments, the nail disorder is not onychomycosis and/or the nail disorder is not induced and/or caused by onychomycosis. In certain embodiments, onychomycosis is not treated using a system and/or method described herein.

In certain embodiments, a system and/or method disclosed herein may be used to treat and/or prevent nail dystrophy (i.e., onychodystrophy) in a nail of a subject. "Nail dystrophy" and "onychodystrophy" as used herein refer to a nail that is poorly formed, misshapen, damaged, and/or discolored. Nail dystrophy may be caused by an endogenous and/or exogenous factor and/or may be a secondary presentation from complete or partial disruption of the nail matrix, proximal nail fold, nail bed, hyponichium, and/or underlying bony phalanx. In some embodiments, nail dystrophy is not induced and/or caused by onychomycosis. In certain embodiments, one or more signs and/or symptoms of nail dystrophy may be treated and/or prevented according to a system and/or method of the present invention. In some embodiments, nail splitting and/or nail fragility may be treated and/or prevented according to a system and/or method of the present invention.

According to some embodiments, the nail disorder may be selected from the group consisting of onycholysis (e.g., distal separation of the nail plate), psoriatic onychorrhexis (e.g., longitudinal grooves and/or ridging of the nail plate), subungual hyperkeratosis (e.g., excessive skin cell growth under nail plate), discoloration, onychoschizia (e.g., peeling of the nail plate surface), lamellar splitting, onychomadesis (e.g., proximal separation of nail plate), brittle nail syndrome, transverse grooves, onychauxis (e.g., nail plate thickening), nail pitting, soft nails, nail dystrophy, nail fragility of intact or damaged nails, and any combination thereof. In certain embodiments, a system and/or method of the present invention may treat and/or prevent nail splitting and/or nail fragility. In some embodiments, a system and/or method of the present invention may prevent direct abrasion and/or friction on a nail surface and/or may provide protection against moisture and/or the effects of moisture. In some embodiments, a system and/or method of the present invention may protect a nail from a subsequent infection (i.e., reinfection) by a fungal disease.

In some embodiments, the nail disorder, such as, but not limited to, nail dystrophy, may or may not be induced and/or caused by an infectious pathogen, such as bacteria, fungi, viruses, parasites, and/or protozoa. In certain embodiments the nail disorder, such as, but not limited to, nail dystrophy, may or may not be induced and/or caused by a fungus. According to some embodiments, a system and/or method of the present invention may prevent a nail disorder induced and/or caused by an infectious pathogen.

Also disclosed herein are systems and/or methods of improving the appearance of a nail compared to the appearance of a nail in the absence of a system and/or method of the present invention. In some embodiments, a system and/or method of improving the appearance of a nail of a subject may comprise topically applying a composition described herein to the nail of the subject, thereby improving the appearance of the nail. In some embodiments, the composition may comprise a poly(urea-urethane)polymer and/or a poly(urea-urethane) pre-polymer. In certain embodiments, the composition may comprise a primary diamine optionally comprising a polyether segment; a secondary aromatic diamine; a polyisocyanate; and optionally, a polyol, and/or a reaction product thereof. In certain embodiments, a system and/or method of the present invention may improve nail growth, color, surface smoothness, shape, and/or thickness of said nail.

In some embodiments, a system and/or method of the present invention may improve the appearance of a nail by increasing or improving nail health compared to nail health in the absence of a method of the present invention. Nail health may be evaluated by how the nail grows, the nail color, the smoothness of the nail, the shape of the nail, and/or the thickness of the nail. For example, the system and/or method may increase or improve nail health by decreasing yellowing and/or discoloration of a nail; decreasing nail dullness; decreasing nail ridges (e.g., longitudinal and/or horizontal ridges), pits, and/or the like; decreasing nail peeling, splitting, cracking, and/or the like; increasing proper nail growth; decreasing nail thickness; decreasing onycholysis; decreasing subungual hyperkeratosis; increasing nail strength; and any combination thereof.

According to some embodiments, a system and/or method of the present invention comprises topically applying a composition described herein to form a coating and/or film. The coating and/or film may adhere to and cover the area of the nail to which it is applied and may prevent or reduce direct abrasion and/or friction on the nail surface. Alternatively or in addition, the coating and/or film may protect the nail from moisture. The coating and/or film may comprise a poly(urea-urethane)polymer and/or a poly(urea-urethane) pre-polymer.

"Nail" as used herein may refer to any part of a fingernail and/or a toenail of a subject. A nail may be a full or partially intact nail. A nail may be a healthy nail, a diseased nail, and/or a damaged nail. A system and/or method disclosed herein may treat a nail disorder in a nail of a subject. In other embodiments a system and/or method disclosed herein may prevent a nail disorder in a nail of a subject. In certain embodiments, a system and/or method disclosed herein may treat and prevent a nail disorder in a nail of a subject. A composition described herein may be applied to all or any portion of a subject's nail. In certain embodiments, a system and/or method may comprise applying a composition described herein to a nail and optionally to the skin surrounding the nail such as, but not limited to, the cuticle.

The present invention finds use in both veterinary and medical applications. Subjects suitable to be treated with a system and/or method of the invention include, but are not limited to, avian and mammalian subjects. Mammals of the present invention include, but are not limited to, canines, felines, bovines, caprines, equines, ovines, porcines, rodents (e.g., rats and mice), lagomorphs, primates (e.g., simians), non-human primates (e.g., monkeys, baboons, chimpanzees, gorillas), and the like. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including, neonatal, infant, juvenile, adolescent, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and canaries). The systems and/or methods of the present invention may also be carried out on animal subjects, particularly mammalian subjects such as mice, rats, dogs, cats, livestock and horses for veterinary purposes and/or for research and development purposes.

In particular embodiments of the present invention, the subject is "in need of" a system and/or method of the present invention, e.g., the subject has been diagnosed with, is at risk for, and/or is believed to have a nail disease or disorder that may be treated using a system and/or method of the present invention. In some embodiments, the subject has a nail disorder, such as, but not limited to, nail dystrophy.

"Treat," "treating" or "treatment of" (and grammatical variations thereof) as used herein refer to any type of treatment that imparts a benefit to a subject and may mean that the severity of the subject's condition is reduced, at least partially improved or stabilized and/or that some alleviation, mitigation or decrease in at least one clinical symptom is achieved and/or there is a delay in the progression of the nail disease or disorder. In particular embodiments, the severity of a nail disorder may be reduced in a subject compared to the severity of the nail disorder in the absence of a method of the present invention. In certain embodiments, a method and/or system of the present invention may treat a subject by improving the appearance of a nail. Improvement in the appearance of a nail may be determined by a visual assessment of the nail, such as by visually assessing the color, surface smoothness, shape, and/or thickness. In some embodiments, a system and/or method of the present invention may improve nail strength compared to the strength of a nail in the absence of a system and/or method of the present invention.

The terms "prevent," "preventing" and "prevention" (and grammatical variations thereof) refer to avoidance, reduction and/or delay of the onset of a nail disease, disorder and/or a clinical symptom(s) in a subject and/or a reduction in the severity of the onset of the nail disease, disorder and/or clinical symptom(s) relative to what would occur in the absence of the systems and/or methods of the invention. The prevention can be complete, e.g., the total absence of the nail disease, disorder and/or clinical symptom(s). The prevention can also be partial, such that the occurrence of the nail disease, disorder and/or clinical symptom(s) in the subject and/or the severity of onset is less than what would occur in the absence of the present invention.

According to some embodiments, a system and/or method of the present invention may comprise applying an effective amount of a composition described herein to a nail. An "effective amount" as used herein, refers to an amount that imparts a desired effect, which may optionally be a therapeutic or prophylactic effect. The effective amount may be a treatment effective amount and/or a prevention effective amount.

A "treatment effective" amount as used herein is an amount that is sufficient to treat (as defined herein) the subject. Those skilled in the art will appreciate that the therapeutic effects need not be complete or curative, as long as some benefit is provided to the subject.

A "prevention effective" amount as used herein is an amount that is sufficient to prevent (as defined herein) the nail disease, disorder and/or clinical symptom in the subject. Those skilled in the art will appreciate that the level of prevention need not be complete, as long as some benefit is provided to the subject.

In certain embodiments, a subject may be in need of a system and/or method of the present invention. The terms "in need of and in need thereof," when used in the context of a composition described herein being applied to a subject, generally refer to a subject who may benefit from a system and/or method of the present invention. A subject in need of a method and/or system of the present invention may be determined by an appropriate healthcare provider. Such judgments may be made based on a variety of factors that are in the realm of expertise of healthcare providers, but include knowledge that the subject has a nail disorder, will develop a nail disorder, or is at risk of developing a nail disorder.

The phrase "therapeutically effective amount" or the like means an amount of a composition described herein that is sufficient to improve the condition, disease, or disorder being treated. Determination of a therapeutically effective amount, as well as other factors related to effective administration of a composition of the present invention to a subject in need of treatment, including frequency of dosing, may depend upon the particulars of the nail disorder that is encountered, including the subject and nail disorder being treated, the severity of the nail disorder in a particular subject, and the frequency of dosing. Determination of a therapeutically effective treatment regimen for a subject is within the level of ordinary skill in the medical or veterinarian arts. In clinical use, an effective amount may be the amount that is recommended by the U.S. Food and Drug Administration, or an equivalent foreign agency.

A system and/or method of the present invention may be carried out for any suitable length of time. In some embodiments, a method and/or system may be carried out until improvement and/or alleviation of at least one sign and/or symptom is observed. In certain embodiments, a system and/or method comprises applying a composition described herein, such as by topical application. The composition may be applied one, two, three or more times per day or may be applied one, two, three, four, five, six, seven or more times per week. In certain embodiments, the composition may be topically applied at least once per week. In other embodiments, the composition may be topically applied at least once per day. In some embodiments, the composition may be topically applied on an as needed basis. The composition may be topically applied at any time of the day. In some embodiments, the composition may be topically applied at bedtime.

A composition described herein may be topically applied by any means. For example, a composition described herein may be topically applied to a nail by painting, coating, dipping, soaking, spraying, and/or the like.

The composition may be configured to form a coating and/or film on the nail after topical application. The coating and/or film may be flexible, waterproof, and/or permeable to water vapor. In some embodiments, the coating and/or film may be colorless and/or transparent. In certain embodiments, the composition may comprise a pigment, colorant, and/or dye and thus the coating and/or film may be colored similar to a fingernail and toenail polish/paint. Exemplary pigments, dyes, and/or colorants include, but are not limited to, those manufactured by HULS AMERICA, INC., known as the 844 Colorant System. Thus, in treating and/or preventing a nail disorder described herein and/or for improving the appearance of a nail, the compositions described herein may be comprise a pigment, dye, and/or colorant and may be used in lieu of a fingernail and toe nail paint.

In some embodiments, a composition of the present invention may comprise at least one antibacterial, antiviral and/or antifungal agent. Exemplary antibacterial agents include, but are not limited to, penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomyein, glycopeptide, glyclyclycline, ketolides, oxazolidinone; imipenen, amikacin, netilmicin, fosfomycin, gentamycin, ceftriaxone, Ziracin, LY 333328, CL 331002, HMR 3647, Linezolid, Synercid, Aztreonam, and Metronidazole, Epiroprim, OCA-9983, GV-143253, Sanfetrinem sodium, CS-834, Biapenem, A-99058.1, A-165600, A-179796, KA 159, Dynemicin A, DX8739, DU 6681, Cefluprenam, ER 35786, Cefoselis, Sanfetrinem celexetil, HGP-3 1, Cefpirome, HMR-3647, RU-59863, Mersacidin, KP 736, Rifalazil, Kosan, AM 1732, MEN 10700, Lenapenem, BO 2502A, NE-1530, PR 39, K130, OPC 20000, OPC 2045, Veneprim, PD 138312, PD 140248, CP111905, Sulopenem, ritipenam acoxyl, RO-65-5788, Cyclothialidine, Sch-40832, SEP-132613, micacocidin A, SB-275833, SR-15402, SUN A0026, TOC 39, carumonam, Cefozopran, Cefetamet pivoxil and T 3811.

Embodiments of the present invention may comprise cleaning the nail prior to and/or after the step of applying the composition described herein to the nail. The nail may be cleaned by washing, soaking, wiping, and/or the like the nail with water, soap and water, and/or a nail polish remover such as, but not limited to, a solution comprising an organic solvent such as acetone. The nail may be cleaned one, two, three or more times per day or one, two, three, four, five, six, seven or more times per week. In certain embodiments, the nail may be cleaned once per week or as needed. The nail may optionally be dried after it is cleaned. In certain embodiments, the nail may be cleaned and optionally dried prior to application with a composition described herein.

Embodiments of the present invention may comprise cleaning a nail prior to application of a composition of the present invention, optionally drying the nail, topically applying a composition of the present invention, and drying the composition to for a coating and/or film. After the coating or film has been formed and is dry, the coating and/or film may be cleaned as needed to remove debris build-up on the nail. The cleaning, however, may not remove the coating and/or film, which may allow for the nail to be protected for a longer duration of time.

In some embodiments, a system and/or method of the present invention may comprise part of a multi-treatment regime. For example, a medicament may be used concurrently with a system and/or method of the present invention to treat an underlying disease and a composition of the present invention may be used to improve the appearance of a nail and/or protect the nail.

In some embodiments, a system and/or method of the present invention may comprise topically applying a composition of the present invention in an amount of about 1 µL to about 15 µL, or any range and/or individual value therein, to a nail and/or the surrounding skin of the nail. In some embodiments, about 1, 2, 3, 4, 5, 6, 7, 8, 9, 10, 11, 12, 13, 14, or 15 µL of the composition may be topically applied to a nail and/or the surrounding skin of the nail. The composition may be topically applied to the nail and/or the surrounding skin of the nail at least once daily. The composition may be topically applied as a thin layer and/or may cover at least a portion of the nail and/or surrounding skin of the nail. In some embodiments, the composition covers the entire nail. The composition may be applied as a thin layer that substantially evenly covers a nail. The composition may be allowed to dry, such as, for example, the composition may be allowed to dry for about 2 to about 3 minutes.

In certain embodiments, the composition may be topically applied to a nail and/or the surrounding skin of the nail in an amount having a weight of about 1 mg to about 10 mg, or any range and/or individual value therein, in some embodiments, about 1, 2, 3, 4, 5, 6, 7, 8, 9, or 10 mg of the composition may be topically applied to a nail and/or the surrounding skin of the nail. Once dry, this may provide a coating and/or film on the nail and/or the surrounding skin of the nail having a weight of about 0.1 rug to about 2 mg, or any range and/or individual value therein, such as, but not limited to, about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 mg.

In some embodiments, the composition may be topically applied to a nail and/or the surrounding skin of the nail at least once daily for at least five consecutive days. An exemplary treatment regime may include: topically applying the composition once daily for five consecutive days; on the sixth day cleaning the nail and/or the surrounding skin of the nail, such as, but not limited to, cleaning with a nail polish remover (e.g., an acetone solution); and on the sixth and seventh days the composition is not applied. Another exemplary treatment regime may comprise topically applying the composition once daily to the nail and/or the surrounding skin of the nail and cleaning the nail and/or the surrounding skin of the nail at least once a week. Either exemplary treatment regime may be repeated for a defined time period (e.g., 2 weeks, a month, etc.) or until improvement and/or alleviation of at least one sign and/or symptom is observed.

Prior to topically applying the composition, loose debris and/or nail material may be removed from the nail and/or the surrounding skin of the nail. Nail clippers and/or a nail file may be used to remove the loose debris and/or nail material.

According to some embodiments of the invention, compositions that may be useful in the systems and/or methods described herein may comprise a poly(urea-urethane) polymer and/or a poly(urea-urethane) pre-polymer. In some embodiments, the composition is a pharmaceutical composition. The term "poly(urea-urethane) polymer" is meant to refer to (i) poly(urea)polymers and (ii) polymers that include both urea (—NRC(=O)NR'—) and urethane (—NR"C(=O)O—) linkages, wherein R, R' and R" are each independently hydrogen; alkyl, as defined herein; or aryl, as defined herein. All polymers herein are described according to the monomer units that react to form the polymer, such as, e.g., polyamines, polyols, polyisocyanates, and the like. The term "polymer" will be understood to include polymers, copolymers (e.g., polymers formed using two or more different monomers), oligomers and combinations thereof, as well as polymers, oligomers, or copolymers that can be formed in a miscible blend.

The term "pre-polymer" refers to a monomer or system of monomers that have been reacted to an intermediate molecular weight state. This material is capable of further polymerization by reactive groups to a fully cured high molecular weight state. As such, mixtures of reactive polymers with unreacted monomers may also be referred to as pre polymers. Typically such pre-polymers are polymers of relatively low molecular weight, usually between that of the monomer and the film polymer or resin. As such, one of skill in the art will appreciate that monomers react to form the poly(urea-urethane) such that the monomer is no longer present once the polymer is formed. However, in some compositions described herein, both monomer and polymer may be present in the formulation prior to curing, and after curing, residual monomer may remain in the cured polymer.

The term "alkyl" refers to a straight, branched or cyclic hydrocarbon. Representative examples of alkyl include, but are not limited to, methyl, ethyl, n-propyl, is propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" is a subset of alkyl and refers to a hydrocarbon group containing from 1 to 4 carbon atoms, Representative examples of lower alkyl include, but are not limited to, methyl, ethyl, n-propyl, iso-propyl, n-butyl, iso-butyl, tert-butyl, and the like. The term "alkyl" is intended to include both substituted and unsubstituted alkyl unless otherwise indicated. Substituted alkyl may be substituted with one or more (e.g., one, two or three) suitable functional groups including, e.g., halo, alkyl, alkoxy, haloalkyl, amino, hydroxyl, aryl, isocyanate, and the like.

The term "alkoxy" refers to the functional group —OR, wherein R is an alkyl, as defined herein.

The terms "aryl" and "arylene" refer to a monovalent or divalent, respectively, monocyclic carbocyclic ring system or a bicyclic carbocyclic fused ring system having one or more aromatic rings. Representative examples of aryl(ene) include, azulenyl(ene), indanyl(ene), indenyl(ene), naphthyl(idene) phenyl(ene), tetrahydronaphthyl(idene), and the like. The term "aryl(ene)" is intended to include both substituted and unsubstituted aryl unless otherwise indicated. Substituted aryl(ene) may be substituted with one or more suitable functional groups (e.g., one, two or three), including, e.g., alkyl and those groups set forth in connection with alkyl above.

The term "polyamine" is meant to refer to compounds having at least two (primary and/or secondary) amine functional groups per molecule.

The term "polyol" is meant to refer to compounds having at least two hydroxyl functional groups per molecule.

The term "polyisocyanate" and "polyisothiocyanate," collectively referred to as "polyiso(thio)cyanate" are meant to refer to compounds having at least two isocyanate or isothiocyanate, respectively, functional groups per molecule.

The terms "pharmaceutical composition" and "medicament" are used interchangeably herein to refer to a composition comprising a therapeutically effective amount of (i) a poly(urea-urethane)polymer according to an embodiment of the present invention, a pharmaceutically acceptable salt thereof and/or monomers thereof and/or a poly(urea-urethane) pre-polymer; (ii) a pharmaceutically acceptable carrier; and (iii) optionally, other additives.

The term "pharmaceutically acceptable salt" refers to a salt or salts prepared from at least one pharmaceutically acceptable non-toxic acid or base including inorganic acids and bases, and organic acids and bases. Pharmaceutically acceptable salts of compounds according to embodiments of the invention include the acid addition and base salts thereof, and may be made using techniques known in the art, such as, but not limited to, reacting the compound with the desired base or acid. Suitable pharmaceutically acceptable base addition salts for compounds according to embodiments of the present invention include metallic salts (e.g., alkali metal salts and/or alkaline earth metal salts) made from aluminum, calcium, lithium, magnesium, potassium, sodium, and zinc; or organic salts made from lysine, N,N'-dibenzylethyl-enediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, formic, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include xinofoate; hydrochloride mesylate, zinc, potassium, or iron salts. In certain embodiments, both water-soluble and water-insoluble salts will be useful based on the mode of administration.

The term "pharmaceutically acceptable carrier" is used herein to refer to a carrier medium that does not significantly alter the biological activity of the poly(urea-urethane) polymer. The one or more substances of which the pharmaceutically acceptable carrier is comprised typically depends on factors (or desired features for its intended use) of the pharmaceutical composition such as the intended mode of administration, desired physical state (e.g., solid, liquid, gel, suspension, etc.), desired consistency, desired appearance, desired taste (if any), desired pharmacokinetic properties once administered (e.g., stability, biological half life), desired release characteristics (e.g., (a) immediate release (e.g., fast-dissolving, fast-disintegrating), or (b) modified release (e.g., delayed release, sustained release, controlled release)), and the like. As known to those skilled in the art, a suitable pharmaceutically acceptable carrier may comprise one or substances, including but not limited to, a diluent, water, buffered water, saline, 0.3% glycine, aqueous alcohol, isotonic aqueous buffer; a water-soluble polymer, glycerol, polyethylene glycol, glycerin, oil, salt (e.g., such as sodium, potassium, magnesium and ammonium), phosphonate, carbonate ester, fatty acid, saccharide, polysaccharide, stabilizing agent (e.g., glycoprotein, and the like for imparting enhanced stability, as necessary and suitable for manufacture and/or distribution of the pharmaceutical composition), excipient, preservative (e.g., to increase shelf-life, as necessary and suitable for manufacture and distribution of the pharmaceutical composition), bulking agent (e.g microcrystalline cellulose, and the like), suspending agent (e.g alginic acid, sodium alginate, and the like), viscosity enhancer (e.g., methylcellulose), taste enhancer (e.g., sweetener, flavoring agent, taste-masking agent), binder (generally, to impart cohesive quality to a tablet or solid formulation; e.g., gelatin, natural and/or synthetic gums, polyvinylpyrrolidone, polyethylene glycol, and the like), extender, disintegrant (e.g., sodium starch glycolate, sodium carboxymethyl cellulose, starch, and the like), dispersant, coating (generally to impart a surface active agent to a tablet or solid formulation; e.g., polysorbate, talc, silicon dioxide, and the like), lubricant (e.g., magnesium stearate, calcium stearate, sodium lauryl sulphate, and the like), or colorant. Other suitable additives include those described elsewhere herein. As known to those skilled in the art, an active ingredient may be flu into a pharmaceutical composition using methods and one or more pharmaceutically acceptable carriers well known in the art, taking the desired features of the pharmaceutical composition, as described above, in mind during formulation. Depending on such desired features, typically a pharmaceutical composition may comprise from about 1% by weight to about 80% by weight of poly(urea-urethane) and from about 10% by weight to about 99% by weight of pharmaceutically acceptable carrier.

According to some embodiments, a system and/or method of the present invention may comprise topically applying a composition comprising a poly(ureaurethane)polymer. The poly(urea-urethane)polymer may be present in the composition in a range of about 10% to about 25% by weight of the composition or any range and/or individual value therein, such as, but not limited to, about 10% to about 20%, about 12% to about 20%, or about 15% to about 20% by weight of the composition. In certain embodiments, the poly(urea-urethane) polymer may be present in the composition in an amount of about 10%, 11%, 12%, 13%, 14%, 15%, 16%, 17%, 18%, 19%, 20%, 21%, 22%, 23%, 24%, or 25% by weight of the composition or any range therein. In some embodiments, the poly(urea-urethane)polymer may be present in the composition in an amount of about 16% by weight of the composition.

The term "bacteria," as used herein, includes any organism from the prokaryotic kingdom, including gram positive and gram negative bacteria. These organisms include genera such as, but not limited to, *Agrobacterium, Anaerobacter, Aqualbacterium, Azorhizobium, Bacillus, Bradyrhizobium, Cryobacterium, Escherichia, Enterococcus, Heliobacterium, Klebsiella, Lactobacillus, Methanococcus, Methanothermobacter, Micrococcus, Mycobacterium, Oceanomonas, Pseudomonas, Rhizobium, Staphylococcus, Streptococcus, Streptomyces, Thermusaquaticus, Thermaerobacter, Thermobacillus* and the like. Exemplary bacteria include those described in United States Patent Application Publication No, 2003/0068808.

The term "virus," as used herein, includes any virus, including double-stranded DNA viruses (e.g., adenoviruses, herpes viruses, poxviruses), single-stranded (+)-sense DNA viruses (e.g., parvoviruses), double stranded RNA viruses (e.g., reoviruses) single-stranded (+)sense RNA viruses (e.g., picornaviruses, togaviruses), single-stranded (−)sense RNA viruses (e.g., orthomyxoviruses, rhabdoviruses), single stranded (+)sense RNA having a DNA intermediate in the lifecycle (e.g, retroviruses), and double stranded DNA with RNA intermediate (e.g., hepadnaviruses). Exemplary viruses include humanpapilloma virus, herpes simplex virus and poxvirus.

The term "fungus," as used herein, includes any fungus or mold, including arbuscular mycorrhiza, conidiophores, chytridiomycota, blastocladiomycota, neocallimastigomycota, zygomycota and glomeromycota. The term also includes slime molds and water molds. Exemplary fungi include candida, malassezia furfur, *Pityrisoporum ovalue*, and dermophytes such as *Trichophyton, Microsporum* and *Epidermophyton*. According to some embodiments of the present invention, provided are polyurea-urethane)polymers that include (a) a primary and/or secondary polyamine; (b) a polyiso(thio)cyanate and/or a derivative thereof; (e) optionally, a polyol; and (d) optionally, additional comonomers.

In some embodiments of the present invention, the poly (urea-urethane)polymer includes an aliphatic primary and/or secondary polyamine. The primary and/or secondary polyamine may also include various other functional groups within the polyamine, including polyether, polyester, polycarbonate and/or polypropylene linkages.

In some embodiments, the polyamine includes a primary diamine that includes at least one polyoxyalkylenediamine. For example, in some embodiments, the polyamine includes a diamine encompassed by Formula 1.

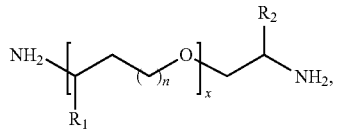

Formula 1 wherein $R_1$ and $R_2$ are each independently hydrogen or alkyl;

n is 0 or a positive integer, such as 1, 2, 3 or 4; and x is a positive integer in a range of 1 to 100, and in some embodiments is 1, 2, 3, 4, 5, 10, 50 or 100. Exemplary primary polyoxyalkylenediamines include Jeffamine® D-2000 polyetheramine, manufactured by Huntsman Petrochemical Corporation and Poly-A® 27-2000, manufactured by Arch Chemicals.

In some embodiments, the polyamine includes an aliphatic secondary diamine that includes an N-alkyl polyoxyalkylenediamine. For example, in some embodiments, the polyamine includes an aliphatic secondary amine encompassed by Formula 2.

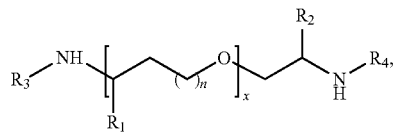

Formula 2 wherein $R_1$ and $R_2$ are each independently hydrogen or alkyl;

$R_3$ and $R_4$ are each independently alkyl or aryl;

n is 0 or a positive integer, such as 1, 2, 3 or 4; and x is a positive integer in a range of 1 to 100, and in some embodiments is 1, 2, 3, 4, 5, 10, 50 or 100.

In some embodiments of the invention, the primary and/or secondary polyamine included in the poly(urea-urethane) may include an aryl(ene) functional group, such as phenyl (ene), naphthyl(idene) and the like. The primary and/or secondary polyamine may also include various other functional groups, such as polyether, polyester, polycarbonate and/or polypropylene linkages.

In some embodiments, the polyamine includes an aromatic primary diamine, such as a compound encompassed by Formula 3.

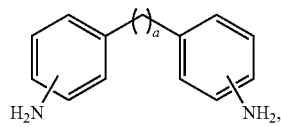

Formula 3 wherein a is a positive integer, such as 1, 2, 3, 4 or 5. In particular embodiments, the primary amine groups are each located on their respective phenyl rings at the para position.

In some embodiments, the polyamine includes an aromatic secondary diamine, such as a compound encompassed by Formula 4.

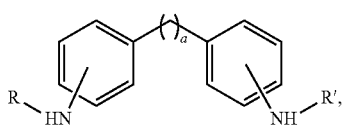

Formula 4 wherein a is a positive integer such as 1, 2, 3, 4 or 5, and R and R' are each independently alkyl or aryl. In particular embodiments, the secondary amine groups are each located on their respective phenyl rings at the para position. Exemplary aromatic secondary diamines include Unilink® 4200, manufactured by Dorf Ketal Chemicals.

As one of ordinary skill in the are will appreciate, mixtures of different types of polyamines may be used in some embodiments of the invention, including mixtures of primary and secondary amines.

According to some embodiments of the present invention, a polyiso(thio)cyanate is included in the poly(urea-urethane) polymer. Any suitable polyiso(thio)cyanate may be included in the composition including, for example, aliphatic polyisocyanates, aromatic polyisocyanates, alicyclic polyisocyanates, heterocyclic polyisocyanates and heteroaromatic polyisocyanates. Exemplary polyisocyanates include polyaryl polyisocyanates as defined in U.S. Pat. No. 2,683,730 tolylene diisocyanate (also referred to as triphenylmethane-4,4'4''-triisocyanate, benzene-1,3,5-triisocyanate; toluene-2,4,6-triisocyanate; diphenyl-2,4,4'-triisocyanate; hexamethylene diisocyanate; xylylene diisocyanate; chlorophenylene diisocyanate; diphenylmethane-4,4'-diisocyanate; naphthalene-1,5-diisocyanate; xylene-alpha, alpha'-diisothiocyanate; 3,3'-dimethyl-4,4'biphenylene diisocyanate; 3-3'dimethoxy-4,4'-biphenylene diisocyanate; 2',3,3'-dimethyl-4,4'-biphenylene diisocyanate; 5,5'-tetramethyl-4,4'biphenylene diisocyanate; 2,2',5,5'-tetramethyl-4,4'biphenylene diisocyanate, 4,4'methylenebis(phenylisocyanate); 4,4'-sulfonylbis (phenylisocyanate); 4,4'-methylene di-orthotolylisocyanate; ethylene diisocyanate; ethylene diisothiocyanate; ethylidene diisocyanate; propylene diisocyanate; butylene diisocyanate; cyclopentylene-1,3-diisocyanate; cyclohexylene-1,4-diisocyanate; cyclohexylene-1,2.diisocyanate, 2,4-tolylene diisocyanate; 2,6-tolylene diisocyanate; 4,4'-diphenylmethane diisocyanate; 2,2-diphenylpropane-4,4'-diisocyanate; p-phenylene diisocyanate; m-phenylene-1,5 diisocyanate; xylylene diisocyanate; 1,4-napthylene diisocyanate; 1,5-naphthylene diisocyanate; diphenyl-4,4' diisocyanate; azobenzene-4,4'-diisocyanate; diphenylsulfone-4,4'-diisocyanate; dichlorohexamethylene diisocyanate; tetramethylene diisocyanate; pentametylene diisocyanate; hexamethylene diisocyanate; 1-chlorobenzene-2,4-diisocyanate; furfurylidene diisocyanate; triphenyl methane triisocyanate; 1,4-tetramethylene diisocyanate; 1,6-hexamethylene diisocyanate; 2,2,4-trimethyl-1,6-hexamethylene diisocyanate; 1,12-dodecamethylene diisocyanate; cyclohexane-1,3(and-1,4)-diisocyanate; 1-isocyanato-2-isocyanatomethyl cyclopentane; 1-isocyanato-3-isocyanatomethyl-3,5,5-trimethyl-cyclohexane (isophorone diisocyanate or IPDI); bis-(4-isocyanatocyclohexyl)-methane; 2,4'dicyclohexyl-methane diisocyanate; 1,3- and 1,4-bis(isocyanatomethyl)cyclohexane; bis-(4-isocyanato-3-methyl-cyclohexyl)-methane, α,α,α',α'-tetramethyl-1,3-1-isocyanato-1-methyl-4(3)-isocyanatomethyl cyclohexane; 2,4-, 1,3- and/or 1,4-phenylene diisocyanate; 2,4- and/or 2,6-toluylene diisocyanate; 2,4- and/or 4,4'-diphenyl-methane diisocyanate; 1,5-diisocyanato naphthalene; aromatic polyisocyanates containing 3 or more isocyanate, groups such as 4,4,4''-triphenylmethane diisocyanate, trimethylenediisocyanate, tetramethylene diisocyanate and hexamethylene diisocyanate; xylene diisocyanate; 1,5-napththylene diisocyanate; 1,4-phenylene diisocyanate; 4,4'-'diphenylmethane diisocyanate (also referred to as "MDI") (Dow's ISONATE® 125M); 4,4'4''-triphenyl-methane triisocyanate; and 3,3'-dimethyl-4,4'-diphenyl-methane diisocyanate; and the like. Aliphatic diisocyanates such as the $C_{36}$ aliphatic diisocyanate derived from the dimer of ricinoleic acid can also be suitably employed and are commercially available, for example, as DD1-1410 (Henkel Corporation, Resin Division, Minneapolis. Minn.). Other examples of polyisocyanates can be found, for example, in *The Development and Use of Polyurethane Products*, E. N. Doyle, McGraw-Hill Book Company, page 27 (1971) and *Polyurethane Handbook*, Gunter Oertel Hauser, Gardner Press (1994).

Mixtures of two or more polyiso(thio)cyanates may also be used. Furthermore, different isomers of the same isocyanate or isothiocyanate may be used. For example, in some embodiments, a mixture (e.g., 80/20 or 65/35 by weight) of 2,4-toluene diisocyanate and 2,6 toluene diisocyanate may be used.

In some embodiments of the invention, the polyiso(thio) cyanates are liquid at ambient temperatures. Liquid polyiso (thio)cyanates may facilitate the production of polymeric products and may obviate the need to melt or dissolve a polyiso(thio)cyanate prior to reacting it. Suitable liquid polyisocyanate materials are known to those of ordinary skill in the art and include, e.g., a liquid polyisocyanate disclosed in U.S. Pat. No. 3,394,164.

Prepolymer polyisocyanates of higher molecular weight (e.g., greater than 500 grams per mole) that have been cleanly stripped allow molecular weight diisocyanate starting materials may be particularly useful in applications wherein the presence of trace diisocyanate monomers may be undesirable in end use applications, e.g., when trace diisocyanate monomers may cause irritation or sensitization.

In particular embodiments of the invention, the polyisocyanate is MDI or a derivative thereof. MDI is a solid with a melting point of 38° C. and may form significant quantities of insoluble dimers when stored above 40° C. Therefore, so-called "modified" MDI derivatives, which are liquid at room temperature and have a reduced tendency to dimerize, may be used, Modified MDIs include those formed by reacting the diisocyanate with a short polyol in a 2:1 diisocyanate to dial ratio, with a short trial in a 3:1 diisocyanate to trial ratio or by converting part of the mixture to a trifunctional carbodiimide-based diisocyanate trimer having the structure of Formula 5. Such an admixture may be obtained from Dow (Liquid MDI, Isonate 143L).

Formula 5

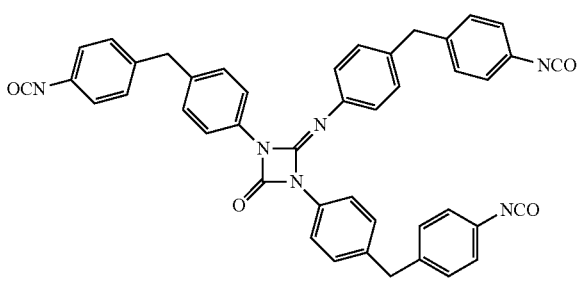

Both of these modifications may provide the MDI with suitable reactivity and a relatively long shelf-life. In some cases, a modified MDI having approximately 2.2 isocyanate groups per molecule may have a shelf life of up to 6 months, in a moisture controlled environment, and at a temperature of between 25° C. and 35° C.

The MDI may also include mixtures of different isomers, including 2,4 and 2,2 isomers. The 2-substituted configuration is typically less reactive than the 4-substituted configuration. The use of different isomers may affect the polymer architecture of the poly(urea-urethane)polymer, and additionally, when a relatively high percentage of MDI isomers is incorporated into the poly(urea-urethane), a lower molecular weight polymer may result. Furthermore, 2,4- and 2,2-linkages may introduce a "kink" or bend hi the polymer chain, which may reduce the tendency of the materials to crystallize. The choice of MDI derivative (e.g., isomer) may affect properties of the solution, the cured film (e.g., curing time), etc. Therefore, the composition of the MDI (or any polyisocyanate/polyisothiocyanate) may be selected as desired for a particular application.

Liquid polyisocyanates may also be formed during the synthesis of MDI. In the production of MDI via the condensation of aniline with formaldehyde, thereby converting the amine groups to the corresponding isocyanate groups, a portion of the initially formed bis adduct of aniline and formaldehyde may further react with the reaction mixture to form polymeric aniline derivatives that may be converted to isocyanates. Typically, such polymeric derivatives will have a functionality of from about 4 to about 15, and in some cases, about 10 isocyanate groups per molecule. Such polymeric polyisocyanates may be obtained after removal of pure MDI by distillation. These polyisocyanate products may be used by themselves or in an admixture with pure MDI. For example, the undistilled reaction mixture of pure MDI with the polymeric. MDI may be used. Such polymeric MDI products are commercially available under such trade designations as RUBINATE® M, RUBINATE® LS-168 and RUBINATE® LF-209 (Huntsman Polyurethanes, Geisman, LA) and PaPI 27, PaPI 135, PaPI 580 and PaPI 901 (Dow, Kalamazoo, Mich.).

In some embodiments of the invention, the polyiso(thio)cyanate component may be present in the form of a polyiso(thio)cyanate adduct. For example, the polyisocyanate may be present as an adduct that includes isocyanurate, uretidione, biuret, urethane, allophanate, carbodiimide and/or oxadiazinetrione groups. In some embodiments the polyisocyanate adducts have an average functionality of 2 to 6 and an NCO content of 5 to 30% by weight. The isocyanatoisocyanurates generally have an average NCO functionality of 3 to 3.5 and an NCO content of 5 to 30%, in some embodiments 10 to 25%, and in particular embodiments, 15 to 25% by weight. In some embodiments of the invention, a mixture of polyisocyanate adducts are present, such as a mixture of isocyanurate and allophanate groups.

According to some embodiments of the invention, the polyiso(thio)cyanate component is present as a prepolymer (hereinafter, collectively referred to as "NCO prepolymer"). Such NCO prepolymers may be prepared from any of the previously described polyiso(thio)cyanates and/or polyiso(thio)cyanurate adducts, in combination with an organic compound that is capable of reacting with the polyiso(thio)cyanates and/or polyiso(thio)cyanurate adducts, in some embodiments, such organic compounds include a polyol, e.g., a polyol described herein. In some embodiments, the prepolymer is formed with an organic compound having a number average molecular weight in a range of 400 to 6000, and in some embodiments, in a range of 800 to 3000. Furthermore, in some embodiments, the prepolymer is formed with an organic compound having a number average molecular weight of less than 400. Such molecular weights may be determined by end group analysis (OH number).

With regard to the organic polyisocyanates, the prepolymers and polyisocyanate adducts, reference is made to U.S. Pat. Nos. 5,516,873 and 6,515,125 and references contained therein.

As one of skill in the art would readily appreciate, mixtures of any of the above polyiso(thio)cyanates, including derivatives thereof, may be incorporated in the poly(urea-urethane)polymers described herein. In particular embodiments, mixtures of MDI and derivatives thereof are utilized, including those mixtures marketed under the tradename Lupranate® (e.g., Lupranate® 81 and 218), manufactured by BASF Aktiengesellschaft.

In some embodiments of the invention, a polyol is not used to form the poly(urea-urethane)polymer. In such a case, a poly(urea) may be formed. However, in some embodiments of the invention, a polyol may be incorporated into the polymer and a poly(urea-urethane)polymer may be formed. For example, in some embodiments, an aliphatic polyol is included in the poly(urea-urethane)polymer. In some embodiments, the aliphatic polyol includes a diol having a structure encompassed by Formula 5.

Formula 5 wherein n is a positive integer. In some embodiments n is a positive integer in a range of 1 to 6, in some embodiments in a range of 5 to 9, and in some embodiments, n is 1, 2, 3 or 4. Exemplary polyols include ethylene glycol, propylene glycol and butylene glycol (such as 1,3-, 1,4- and 2,3-butylene glycol).

In some embodiments, the polyol includes a diol having a structure encompassed by Formula 6.

Formula 6 wherein p is a positive integer, and R and R' are each independently hydrogen or alkyl. In some embodiments, p is an integer in a range of 1 to 100, in particular embodiments, p is 1, 2 or 3; and in particular embodiments p is 4 or more. Exemplary polyols include polyethylene glycol and polypropylene glycol having various molecular weights (e.g., 200, 400, 600, 1000). Other polyols include trimethylol propane and those marketed under the name Multranol® (e.g, Multranol® 4012), manufactured by Bayer Material Science.

As one of ordinary skill in the art will appreciate, mixtures of polyols may be used in some embodiments of the invention, in particular embodiments, ethylene glycol and propylene glycol are provided in equal amounts. Additionally, as described above, in particular embodiments, polyols may be used to form prepolymers with the polyiso(thio)cyanates.

In some embodiments of the invention, other comonomers may be reacted with the polyamines, (optionally) polyols and poly(iso)thiocyanates and become incorporated into the poly(urea-urethane)polymer. For example, in some embodiments, siloxanes may be incorporated into the poly (urea-urethane). Siloxane segments may impart additional water resistance and flexibility to the coating. Additionally, siloxanes such as poly(dimethyl siloxane) may be used to treat burns, and so incorporating such materials into the poly(urea-urethane) may provide additional beneficial properties to the coatings. Such siloxane segments may be introduced into the poly(urea-urethane) by incorporating siloxane containing polyols, polyamines, polyisocyanates, alcohols, amines and isocyanates into the reaction mixture. Exemplary polyols and polyamines may be found in U.S. Pat. Nos. 3,384,599, 4,737,558, 4,962,178, 4,942,212, 5,221,724, 5,430,121, 5,589,563 and 5,196,458.

Fluorinated comonomers may also be included in the poly(urea-urethane) polymer, according to some embodiments of the invention, Fluorinated segments incorporated into the polyurea/urethane polymer may impart additional water resistance/repellency, and may also impart hydrocarbon resistance and/or low surface tension materials, in embodiments wherein such characteristics are desirable. Such fluorinated segments may be introduced into the poly (urea-urethane) by incorporating fluorine containing polyols polyamines, polyisocyanates, alcohols, amines and isocyanates into the reaction mixture. Such fluorinated comonomers are known to those skilled in the art. Exemplary fluorinated comonomers include those described in U.S. Pat. No. 5,453,540, EP 0446796B1 and WO 2007/011593A1.

The poly(urea-urethane)polymers according to embodiments of the invention may be prepared using any suitable technique known to those of skill in the art. As such, the polymerization methods may be homogenous or heterogeneous, including, e.g., solution, precipitation, suspension and emulsion polymerization methods. Such polymerization techniques are described in further detail in *Principles In Polymerization*, by George Odian (Wiley-Interscience, 4$^{th}$ ed. 2004). Specific examples of heterogeneous polymerizations including isocyanate-based polymerizations to form polyureas and polyurethanes, and related polymers, may be found in U.S. Pat. Nos. 4,107,256 and 6,197,878.

Depending on the polymerization method utilized, additional surfactants or stabilizers may necessary in order to prevent agglomeration or precipitation. Such additives are well-known to those of skill in the art and may be chosen so as to be chemically incorporated (e.g., covalently linked) into the poly(urea-urethane)polymer. Such additives may also be chosen so as to avoid reactivity with the monomers employed in the formulation.

The order and rate of adding the polyamines, polyols, additional monomers and polyiso(thio)cyanates may substantially alter the final architecture of the resulting prepolymer. As such, various preparations may be used to achieve the desired polymer structure. In some embodiments of the invention, the polyamine, polyol, polyisocyanate and additional comonomers may be added to a solvent at one time, or may be added in a particular order. Toward this end, in some embodiments, one or more of the monomers may be added to the reaction mixture in a continuous addition mode (e.g., via batch, semi-hatch or continuous polymerization methods). Additionally, under some circumstances, specific combinations of monomers, such as polyamines and polyisocyanates, or polyols and polyisocyanates, may be reacted in a first step to form a polymeric isocyanate prepolymer. Such prepolymer synthesis may allow for the further control of polymer architecture, solubility or allow for tailoring of the properties of the final polymer surface. In particular embodiments of the invention, all polyamine and polyol monomers are added to a solvent in a first step and then the isocyanate is added in a second step. In such circumstances, the isocyanate will react and incorporate the polyamines and polyols in a statistical fashion according, to their relative reactivity.

Catalysts may be added to the polymerization mixture in order to increase or otherwise control polymerization or curing rates. Such catalysts are known to those of skill in the art, and include, e.g., the catalysts described in U.S. Pat. No. 4,960,620. The polyamines and polyols may react with the polyisocyanate at room temperature. However, in some embodiments, the reaction medium can be heated to facilitate the reaction.

In some embodiments of the invention, provided are pharmaceutical compositions that include (a) at least one polyurea-urethane)polymer according to an embodiment of the present invention, a pharmaceutically acceptable salt thereof and/or monomers thereof; (b) a pharmaceutically acceptable carrier; and (c) optionally, other additives.

Any of the polyurea or polyurea-urethane)polymers described herein may be included in a composition, such as a pharmaceutical composition, for use in a system and/or method according to embodiments of the invention. In addition, monomers that will form such polymers upon curing may also be included in a composition according to embodiments of the invention. Furthermore, mixtures of any polyurea polymer, poly(urea-urethane) polymer and monomers thereof may also be present in compositions according to embodiments of the invention.

According to some embodiments of the invention, poly (urea/polyurethane) compositions include a pharmaceutically acceptable carrier. In some embodiments, the pharmaceutically acceptable carrier is a solvent that can completely dissolve the monomers (polyamines and polyiso(thio)cyanates, and optionally, polyols and additional comonomers). Additionally, in some embodiments, the pharmaceutically acceptable carrier will reduce the reaction between the reactive groups in the poly(urea-urethane) monomers and/or reduce or prevent the poly(urea-urethane) from solidifying or gelling until the desired time, such as when the solvent is removed from the solution, e.g., via evaporation.

In particular embodiments of the invention, the pharmaceutically acceptable carrier includes a solvent such as an aldehyde; ketone; ester; ortho, meta, or para-dimethylbenzene; N-methylpyrrolidone; Solvesso solvent; a hydrocarbon solvent, such as a petroleum hydrocarbon solvent; a lactone; a siloxane, or a mixture of any of the above. Additional solvents may be found in U.S. Patent Publication Nos. 2006/021627, and U.S. Publication No. 2006/008856A1 and U.S. Pat. Nos. 3,577,516, 4,987,893, 5,103, 812, 6,458,376, 6,994,863, 5,874,481.

In some embodiments, an aldehyde or ketone solvent has a structure encompassed by Formula 7.

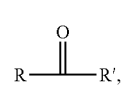

Formula 7 wherein R and R' are each independently selected from hydrogen and alkyl. In some embodiments, the alkyl may include 1, 2, 3 or 4 carbon atoms. In some embodiments, R and R' together form a ring, such as a five or six membered ring. Exemplary ketones include acetone, methylethylketone (MEK), methylisobutylketone and N-methylcyclohexanone. Exemplary aldehydes include acetaldehyde, propionaldehyde, butyraldehyde and isobutyraldehyde.

As an additional example, in some embodiments, an ester solvent has a structure encompassed by Formula 8.

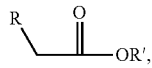

Formula 8 wherein R is hydrogen, alkyl (such f is an alkyl including 1, 2, 3 or 4 carbon atoms) or alkoxy (such as an alkoxy that includes 1, 2, 3 or 4 carbon atoms); and R is an alkyl group (such as an alkyl that includes 1, 2, 3 or 4 carbon atoms). In some embodiments, R and R' together form a ring, such as a ring that includes 2, 3, 4 or 5 carbon atoms. Exemplary ester solvents include methyl acetate, ethyl acetate, butyl acetate, and methyl propyl acetate.

In particular embodiments of the invention, siloxane-based solvents, such as hexamethyldisiloxane, pentamer cyclomethicone tetramer cyclomethicone and mixtures thereof can be employed in poly(urea-urethane) compositions of the invention. Other suitable siloxane solvents are described in U.S. Publication No 2007/0041935 to Salamone et al., U.S. Pat. No. 6,280,752 to Paulo, U.S. Pat. No. 5,582,815 to Appino and U.S. Pat. No. 5,738,857 to Sejpka.

According to some embodiments of the invention, the compositions described herein may include other additives, including, but not limited to, catalysts, UV absorbers, fillers, plasticizers, blowing agents, rheology modifiers, viscosity enhancers, adhesion promoters and those described in U.S. Patent Application Publication No. 2006/0216267. Other additives are described elsewhere herein.

As described above, the carrier can be in a wide variety of forms, such as sprays, emulsions, mousses, liquids, creams, oils, lotions, ointments, gels and solids. In the case of a solution, it can be lyophilized to a powder and then reconstituted immediately prior to use. For dispersions and suspensions, appropriate carriers and additives include aqueous gums, celluloses, silicates or oils.

In particular embodiments, suitable pharmaceutically acceptable topical carriers include, but are not limited to, water, glycerol, alcohol, propylene glycol, fatty alcohols, triglycerides, fatty acid esters, and mineral oils. Suitable topical cosmetically acceptable carriers include, but are not limited to, solutions, emulsions, dispersions, suspensions, syrups, elixirs, and the like with suitable carriers and additives being water, alcohols, oils, glycols, preservatives, flavoring agents, coloring agents, suspending agents, petroleum jelly, petrolatum, mineral oil, vegetable oil, animal oil, organic and inorganic waxes, such as microcrystalline, paraffin and ozocerite wax, natural polymers, such as xanthanes, gelatin, cellulose, collagen, starch or gum arabic, synthetic polymers, alcohols, polyols, and the like. Preferably, because of its non-toxic topical properties, the pharmaceutically and/or cosmetically-acceptable carrier u substantially miscible in water. Such water miscible carrier compositions can also include sustained or delayed release carriers, such as liposomes, microsponges, microspheres or microcapsules, aqueous based ointments, water-in-oil or oil-in-water emulsions, gels and the like.

In addition to liquids, the compositions according to embodiments of the invention may be provided in an aerosol or non-aerosol spray. The aerosol spray, whether formed from solid or liquid particles, can be produced by the aerosol generator. Any suitable propellant may be used in carrying out the present invention. Particularly, formulations to be applied in spraying forms such as dispersible concentrates or powders may contain surfactants such as wetting and dispersing agents, e.g., the condensation product of formaldehyde with naphthalene sulphonate, an alkylarylsulphonate, a lignin sulphonate, a fatty alkyl sulphate, and ethoxylated alkylphenol and an ethoxylated fatty alcohol.

In particular embodiments, formulations suitable for topical application to a nail can take the form of an ointment, cream, lotion, paste, gel, solution, spray, aerosol, or oil. Carriers that can be used include petroleum jelly, lanoline, polyethylene glycols, alcohols, transdermal enhancers, and combinations of two or more thereof.

According to some embodiments of the present invention, pharmaceutical compositions may be formulated as single component formulations. The term "single component," as used herein, refers to a one pot formulation that does not require a curing agent or accelerant in order to cure the formulation and form a film. Instead, the formulation can be administered to a subject in need thereof in the manner in which it is stored, without combining or mixing the formulation with another component.

Such single component formulations may be obtained by reducing the reactivity of the components in the formulation. In order to achieve this, the single component formulations can be prepared by judicious selection of the appropriate amounts of each component, as well as the appropriate amount and type of solvent. For example, in some embodiments, the solvent is present in the formulation in an amount in a range of about 10 weight percent and about 95 weight percent, in particular embodiments, the solvent is present in the formulation in an amount in a range of about 50 weight percent and about 90 weight percent. Furthermore, in some embodiments, the polyamine component includes a secondary polyamine in an amount in a range of about 0.5 weight percent and 5 weight percent. Additionally, the particular polyiso(thio)cyanates included may also affect the reactivity and so particular polyiso(thio)cyanates are useful for achieving single component formulations. For example, modified MDI poly having higher percentages (e.g., in a range of 10% and 40%) 2-substituted phenyl isocyanate groups, such as modified MDI polyisocyanates including Lupranate® 218 and Lupranate® 81, may be used.

In some embodiments, the amount of solvent employed is that which is sufficient to dissolve a first set of reactants (polyamines and optionally polyols and any additional comonomers) with the polyiso(thio)cyanate second reactant, and allow for the reaction product thereof, i.e., the poly (urea-urethane) to remain in solution without precipitation or gelling. Typically, the amount of solvent employed is about 10 to 80% of the total reaction solution volume. The amount of solvent is adjusted depending upon the viscosity desired for specific application requirements. Typically, the reaction product viscosity will range from about 0.05 centipoise to about 1800 centipoise at room temperature.

According to some embodiments of the invention, the single component poly compositions can be stored for a relatively long period of time, e.g. greater than 3 months at 25° C. without exhibiting precipitation or gelling, greater than 6 months at 25° C. without precipitation or gelling, greater than 1 year at 25° C. without precipitation or gelling, or even greater than 2 years at 25° C. without precipitation or gelling. Accordingly such compositions can be applied in any manner that allows for the removal of at least a portion of the pharmaceutically acceptable carrier, leading to the formation of a solid, cured poly(urea-urethane) material.

While the process and the single pot formulation permits the production of polymeric materials without the use of blocking agents, end-capping chemical modifications or thermally activated catalysts, e.g. caprolactum, B-carbonyl compounds (such as ethyl aceto acetate, ethyl malonate), alcohols and oximes; polymerization additives of various types employed in the manufacture of polymeric products can desirably be employed. For example, such polymerization agents as catalysts, ultraviolet absorbers, fillers, plasticizers, blowing agents, etc., can be employed where desired. Further information on such additives may be found in U.S. Patent Publication No. 2006/0216267 and elsewhere herein.

The present invention is explained in greater detail in the following non-limiting Examples.

EXAMPLES

Example 1

Exemplary compositions of the present invention are provided below. All component amounts are identified in terms of stoichiometrically balanced volume amounts expressed as milliliters. Liquid thermosetting, hydrophobic, elastomeric, non-toxic polymer solution compositions were prepared by adding the reactants in the sequence given. Solutions were stir-blended constantly at 20 paddle revolutions per minute during the sequential addition of the ingredients, and for 15-20 minutes after addition of the last ingredient. These parameters of the stir-blending process, in terms of revolutions and time, are the most optimum for obtaining maximum sequential reactivity of the ingredients during blending. The sequential mixing process was done at ambient conditions of 70-80° Fahrenheit, about 750-760 mm Hg, and relative humidity of 50-65%.

Treatment Device Formulation #1 Working Identifier: PMS-1 P-1000

| Reagent | Volume [ml] | Stoichiometric Volume Ratio |
|---|---|---|
| Acetone | 240 | 0.505 |
| Acetate | 126.75 | 0.267 |
| Versalink ® P-1000 polyurethane additive | 55.5 | 0.117 |
| Ethyl Glycol | 7.5 | 0.016 |
| Propylene Glycol | 7.5 | 0.016 |
| Rubinate ® 9259 or 2143 polyurethane aromatic secondary diamine | 37.5 | 0.079 |
| Total: | 474.75 | 1.000 |

Treatment Device Formulation #2 Working Identifier: PMS-3

| Reagent | Volume [ml] | Stoichiometric Volume Ratio |
|---|---|---|
| Acetone | 2888 | 0.752 |
| Acetate | 228 | 0.059 |
| Jeffamine ® D-2000 polyetheramine | 304 | 0.080 |
| Unilink ® 4200 aromatic diamine | 76 | 0.020 |
| Multranol ® 4012 polyol | 144 | 0.038 |
| No. 218 Isocyanate | 198 | 0.051 |
| Total: | 3838 | 1.000 |

Treatment Device Formulation #3 Working Identifier: PMS-1 White

| Reagent | Volume [ml] | Stoichiometric Volume Ratio |
|---|---|---|
| Acetone | 132 | 0.697 |
| Mineral Spirits | 44 | 0.232 |
| 4012 | 2.2 | 0.012 |
| Jeffamine ® D-2000 polyetheramine | 8.8 | 0.046 |
| No. 218 Isocyanate | 2.4 | 0.013 |
| Total: | 189.4 | 1.000 |

Additional formulations of exemplary compositions of the present invention are presented below.

Formulations of Working Identifier PMS-1

| Reagent | Volume [ml] | Volume Ratio | Volume [ml] | Volume Ratio | Volume [ml] | Volume Ratio |
|---|---|---|---|---|---|---|
| Acetone | 106.8 | 0.702 | 132.0 | 0.697 | 132.0 | 0.705 |
| Mineral Spirits | 35.6 | 0.234 | 44.0 | 0.232 | 44.0 | 0.235 |
| Jeffamine ® D-2000 polyetheramine | 6.6 | 0.043 | 8.8 | 0.046 | 8.8 | 0.047 |
| Unilink ® 4200 aromatic diamine | 1.2 | 0.008 | — | — | — | — |
| 4012 | — | — | 2.2 | 0.012 | — | — |
| No. 218 Isocyanate or Lupranate ® 81 Isocyanate | 2.0 | 0.013 | 2.4 | 0.013 | 2.4 | 0.013 |
| Total | 152.2 | 1.000 | 189.4 | 1.000 | 137.2 | 1.000 |

Formulations of Working Identifier: PMS-3

| Reagent | Volume [ml] | Volume Ratio | Volume [ml] | Volume Ratio |
|---|---|---|---|---|
| Acetone | 650.0 | 0.776 | 850.0 | 0.782 |
| MEK | 50.0 | 0.059 | 100.0 | 0.092 |
| Jeffamine ® D-2000 polyetheramine | 60.0 | 0.071 | 60.0 | 0.055 |
| Unilink ® 4200 aromatic diamine | 15.0 | 0.020 | 15.0 | 0.014 |
| 4012 | 20.0 | 0.024 | 20.0 | 0.018 |
| Ethyl Glycol | 5.0 | 0.006 | 5.0 | 0.005 |
| Propylene Glycol | 5.0 | 0.006 | 5.0 | 0.005 |
| Lupranate ®81 Isocyanate | 32.0 | 0.038 | 32.0 | 0.029 |
| Total | 837 | 1.000 | 1087 | 1.000 |

The compositions of the present invention have the following physiological properties.
1. Non-Cytotoxic, MEM Elusion—MG 023-0 Dilution
2. Non-Hemolytic—In Vitro
3. Non-Pyrogenic—Test T 10, Material Mediated
4. Non-Carcinogenic—Standard Ames *Salmonella* Tests Example 2

For each of Examples 2-12, the reagents are added in the order given with stirring for approximately 5 minutes in between reagent additions. The MDI is added last and is added slowly with stirring. The reactions were maintained at room temperature, ca. 70° C., throughout the reaction. After isocyanate addition was complete, the reactions were stirred for approximately 10 minutes and then transferred to sample jars for storage prior to being characterized using a combination of High Performance Liquid Chromatography (HPLC), Gel Permeation Chromatography (GPC), Gel Permeation Chromatography with Multi Angle Light Scattering detection (GPC-MALS), Nuclear Magnetic resonance (NMR) Spectroscopy to Fourier Transform Infra Red (FT-IR) Spectroscopy to determine molecular weight, verify chemical structure and verify reaction completion.

| | |
|---|---|
| Acetone | 850 ml |
| Methyl Ethyl Ketone | 100 ml |
| Polyetheramine; D-2000 | 60.0 ml |
| Secondary Diamine; UOP 4200 | 15.0 ml |
| Polyether Polyol; Multranol 4012 | 20.0 ml |
| Ethylene Glycol | 5.0 ml |
| Propylene Glycol | 5.0 ml |
| MDI Lupranate 5143 | 32.0 ml |

The resulting product was a clear, off white solution from which a small amount of white solid precipitated and settled to the bottom of the reaction flask. FT-IR spectroscopy and NMR spectroscopy were used to validate structure and showed that only a small portion of isocyanate groups are present in the reactive prepolymer. GPC characterization resulted in polystyrene equivalent number average molecular weight of 1,990 g/mol, weight average molecular weight of 6,910 g/mol and polydispersity index of 3.5. No peaks corresponding to residual starting material were observed in the chromatogram.

Example 3

| | |
|---|---|
| Acetone | 212.5 ml |
| Methyl Ethyl Ketone | 25 ml |
| Polyetheramine; D-2000 | 15.0 ml |
| Secondary Diamine; UOP 4200 | 3.75 ml |
| Polyether Polyol; Multranol 4012 | 5.0 ml |
| Ethylene Glycol | 1.25 ml |
| Propylene Glycol | 1.25 ml |
| MDI; Lupranate 81 | 8.0 ml |

The resulting product was a clear, off white solution from which a small amount of white solid precipitated and settled to the bottom of the reaction flask, FT-IR spectroscopy and NMR spectroscopy were used to validate structure and showed that only a small portion of isocyanate groups are present in the reactive prepolymer. GPC characterization resulted in polystyrene equivalent number average molecular weight of 1,960 g/mol, weight average molecular weight of 9120 g/mol and polydispersity index of 4.6. No peaks corresponding to residual starting material were observed in the chromatogram.

Example 4

| | |
|---|---|
| Acetone | 212.5 ml |
| Methyl Ethyl Ketone | 25 ml |
| Polyetheramine; D-2000 | 15.0 ml |
| Secondary Diamine; UOP 4200 | 3.75 ml |
| Polyether Polyol; Multranol 4012 | 5.0 ml |
| Ethylene Glycol | 1.25 ml |
| Propylene Glycol | 1.25 ml |
| MDI; Lupranate 81 | 8.0 ml |

The resulting product was a clear, off white solution from which a small amount of white solid precipitated formed and settled to the bottom of the reaction flask. FT-IR spectroscopy and NMR spectroscopy were used to validate structure and showed that only a small portion of isocyanate groups are present in the reactive prepolymer. GPC characterization resulted in polystyrene equivalent number average molecular weight of 1,740 g/mol, weight average molecular weight of 3,110 g/mol and polydispersity index ($M_w/M_n$) of 1.8. No peaks corresponding to residual starting material were observed in the chromatogram.

Example 5

In this example, the polyetheramine, D-2000, was first dissolved in a mixture of 400 ml acetone and 50 ml Methyl ethyl ketone. The MDI, Lupranate 5143, 32.0 ml was then added slowly in order to form a polyether amine prepolymer adduct. The remaining acetone and methyl ethyl ketone are placed in a second reaction flask and the remaining reagents added in turn with stirring. Once the remaining co-monomers were all dissolved the polyetheramine/MDI prepolymer adduct was added slowly to the second reaction flask. The resulting formulation was clear with a slightly yellow tint.

| | |
|---|---|
| Acetone | 850 ml |
| Methyl Ethyl Ketone | 100 ml |
| Polyetheramine; D-2000 | 60.0 ml |
| Secondary Diamine; UOP 4200 | 15.0 ml |
| Polyether Polyol; Multranol 4012 | 20.0 ml |
| Ethylene Glycol | 5.0 ml |
| Propylene Glycol | 5.0 ml |
| MDI Lupranate 5143 | 32.0 ml |

Example 6

A formulation according to Example 2 was carried out by pre-reacting Lupranate 5143 and polyether diamine D-2000 in 400 ml of acetone. The resulting solution was then added slowly to the remaining ingredients. A cloudy poly(urethane-urea) solution resulted.

Example 7

A formulation according to Example 2 was carried out, except that MEK was replaced by an equal amount of acetone.

Example 8

A formulation according to Example 2 was carried out, except that one-half of the ethylene glycol and one half of the propylene glycol were each replaced with a stoichiometrically equivalent amount of polyetherdiamine D-2000.

Example 9

A poly(urea-urethane) formulation prepared according to Example 2 was evaluated for drug delivery potential using in vitro release testing (IVRT) with hydrocortisone medicament FIG. 1 shows that a film formed from a single application of the formulation, allows hydrocortisone to readily pass through it. This result demonstrates that the poly(urea-urethane) film allows transport of medicaments.

Example 10

Figure 2:
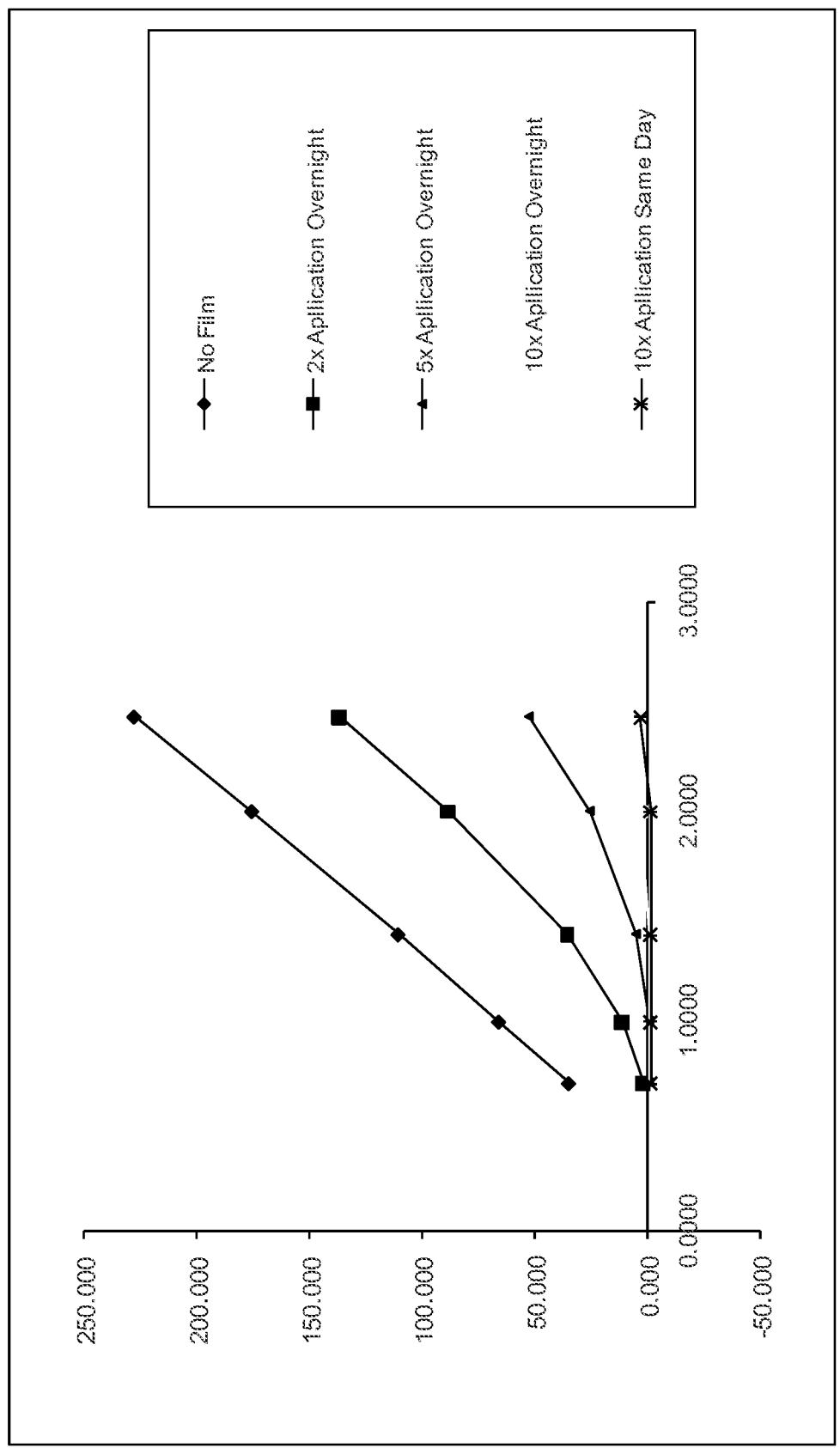
FIG. 2 shows a graph illustrating the release rate of a formulation comprising a hydrocortisone medicament according to embodiments of the invention.

A poly(urea-urethane) formulation prepared according to Example 2 with a hydrocortisone medicament was painted on a membrane surface 2×, 5×, and 10× in 5 minute intervals. The resulting films were evaluated using in vitro release testing (TVRT). Results are shown in FIG. 2. The release of hydrocortisone is predictable and is inversely proportional to the number of applications (and hence film thickness). Thus the release rate of the drug can be controlled by film thickness. These results indicate that the polymer film can incorporate an agent (drug) into its matrix and release it at a constant rate.

Example 11

Water vapor transmission testing was conducted on films cast from a poly(urea urethane) formulation prepared according to Example 2. Tests were carried out in accordance with test method ASTM E 96/E 96M-05 as follows: Aluminum cups were filled with water to within 19±6 mm of the top, and the sample films were sealed across the cup mouth. Three replicates of each specimen were run. The samples were placed in a sealed chamber with a saturated solution of magnesium nitrate to maintain a controlled humidity. The temperature and humidity were recorded with a solid state sensor, and the cups were weighed periodically (every three and four days, alternately) until a steady rate for mass loss was observed. The average temperature over the testing was approximately 23° C., and the average humidity in the chamber was 74%.

The permeance of the film samples was calculated from the mass loss rate, temperature, humidity, cup dimensions, and film thickness and are given in Table 1. The edge mask, still air resistance, and surface resistance corrections were applied to the raw values obtained. The water transmission rate was high enough that buoyancy correction is not necessary. Results clearly indicate that the film allows the passage of water vapor sufficient to aid in wound healing.

TABLE 1

Water Vapor Transmission results for poly(urea-urethane) film samples.

| Sample | Permeance (ng s$^{-1}$ m$^{-2}$ mmHG$^{-1}$) |
|---|---|
| 1 | 864 |
| 2 | 667 |
| 3 | 892 |
| 4 | 851 |

Example 12

A poly(urea-urethane) formulation sample prepared according to Example 2 was tested for systemic toxicity [acute, injection] in accordance with test method ANSI/AAMI/ISO 10993-11; 3-day gross observations of toxicity in mouse after single IP injection of 70° C./24 hr saline and vegetable oil extracts; five albino naïve mice per extract, five mice per control.

Acceptance Criteria: The test article meets the USP requirements if none of the animals treated with the test article extract show a significantly greater biological reactivity than those treated with the control.

Results: The test article met the requirements of the USP Systemic Injection test using the extracting media and conditions listed, as no significant biological reactivity was observed.

Example 13

A multi-center, single-arm, self-controlled clinical trial was performed. A total of 63 subjects were enrolled and 53 subjects completed the trial. The subject population included 50 males and 13 females with a mean age of 51 years. The inclusion criteria were having a nail fungal infection (*Trichophyton* (n-62) or *Epidermophyton* (n=1)) of at least one great toe by visual assessment and positive dermatophyte culture, with 20% to 65% nail involvement, and the exclusion criteria were having a nail thickness >3 mm or chronic disease that would decrease circulation to extremities.

The subjects were assessed before treatment and at 1, 3, and 6 months time points by visual and culture methods. Further follow-up of patients was voluntary, but continued to one year, to determine infection recurrence rates or longer-term AE. Due to the nature of the product, there was no blinding of the application procedure. The primary efficacy endpoint was clearance of fungal nail infection, defined by negative culture, within the six-month treatment phase. The subjects were self-treated with a 16% by weight poly(urea-urethane)polymer solution. The treatment regimen was weekly topical application of the solution to the nail having the fungal infection for six months.

In comparisons of total visual parameters (e.g color, nail involvement, onycholysis, thickness of nail plate, and subungual hyperkeratosis) at baseline to those at the 6-month assessment, 17% had no change from baseline, 23% showed overall deterioration, whereas 60% showed improvement in visual nail characteristics. There was an average 20% improvement for all subjects in all visual parameters (color 10%, onycholysis 30%, all others 20%) over the six months of the study. The results from the visual assessment are summarized in Table 2.

TABLE 2

Change in visual assessment parameters from baseline to six-month follow-up visit.

|  | Color | Nail Involvement | Onycholysis | Thickness | Subungual Hyperkeratosis |
|---|---|---|---|---|---|
|  | Number (percentage) of total subjects | | | | |
| Deterioration | 7 (13%) | 6 (11%) | 5 (9%) | 2 (4%) | 8 (15%) |
| No change | 30 (57%) | 21 (40%) | 28 (53%) | 33 (62%) | 25 (47%) |
| Improvement | 16 (30%) | 26 (49%) | 20 (38%) | 18 (34%) | 20 (38%) |

For patients tracked for 6 months after the treatment period, the fungal infection recurrence rate was less than 24%. Based on the literature, it is believed that for fungal infections there is a 40-60% recurrence rate for marketed products.

Although the present invention has been described herein with respect to particular features, aspects and embodiments thereof, it will be apparent that numerous variations, modifications, and other embodiments are possible within the broad scope of the present invention, and accordingly, all variations, modifications and embodiments are to be regarded as being within the scope of the invention. The present embodiments are therefore to be construed in all aspects as illustrative and not restrictive and all changes coming within the meaning and equivalency range of the appended claims are intended to be embraced therein.

That which is claimed is:

1. A method of treating onychodystrophy, where the onychodystrophy is not caused by onychomycosis, in a subject comprising:
   topically applying a composition comprising a poly(urea-urethane) to a nail of said subject wherein the composition forms a film permeable to water vapor.

2. The method of claim 1, wherein said step of topically applying is carried out at least once per week.

3. The method of claim 1, wherein said composition comprises said poly(urea-urethane) polymer in a range of about 10% to about 25% by weight of the composition.

4. The method of claim 1, wherein said step of topically applying said composition comprises:
   providing said composition in the form of a solution; and
   coating said nail of said subject with said solution.

5. The method of claim 1, wherein the composition further comprises a secondary aromatic diamine.

6. The method of claim 1, wherein the composition comprises a polyisocyanate.

7. The method of claim 6, wherein the polyisocyanate comprises MDI.

8. The method of claim 1, wherein the composition comprises a polyol.

9. The method of claim 1, wherein the composition comprises at least one ketone solvent.

10. The method of claim 1, wherein the composition comprises a dye, colorant, and/or pigment.

11. The method of claim 1, wherein said composition comprises an antibacterial, and/or antiviral medicament.

12. The method of claim 1, wherein the nail is a diseased nail.

* * * * *